US010052432B2

(12) United States Patent
Dexter et al.

(10) Patent No.: US 10,052,432 B2
(45) Date of Patent: Aug. 21, 2018

(54) IRRIGATION SYSTEM AND CLIP FOR A SURGICAL INSTRUMENT

(71) Applicant: Medtronic PS Medical, Inc., Fort Worth, TX (US)

(72) Inventors: S. Shane Dexter, Keller, TX (US); R. Mitchell Sherry, Fort Worth, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 302 days.

(21) Appl. No.: 14/968,069

(22) Filed: Dec. 14, 2015

(65) Prior Publication Data

US 2016/0095974 A1 Apr. 7, 2016

Related U.S. Application Data

(63) Continuation of application No. 13/242,106, filed on Sep. 23, 2011, now Pat. No. 9,211,373.

(51) Int. Cl.
*A61M 3/02* (2006.01)
*A61B 17/14* (2006.01)
*A61B 17/32* (2006.01)

(52) U.S. Cl.
CPC ........... *A61M 3/0279* (2013.01); *A61B 17/14* (2013.01); *A61B 2017/320084* (2013.01); *A61B 2217/007* (2013.01); *A61B 2218/002* (2013.01)

(58) Field of Classification Search
CPC .. A61B 2017/320084; A61B 2217/007; A61B 2218/002; A61B 17/14; A61M 3/0279
See application file for complete search history.

(56) References Cited

U.S. PATENT DOCUMENTS

| 2,012,886 A | 8/1935 | Lowry |
| 3,949,753 A | 4/1976 | Dockhorn |
| 4,634,420 A | 1/1987 | Spinosa et al. |
| 4,747,820 A | 5/1988 | Hornlein et al. |
| 4,846,790 A | 7/1989 | Hornlein et al. |
| 4,881,761 A | 11/1989 | Hornlein et al. |
| 4,941,872 A | 7/1990 | Felix et al. |
| 4,988,334 A | 1/1991 | Hornlein et al. |

(Continued)

OTHER PUBLICATIONS

European Office Action dated Mar. 22, 2017 for European Application No. 12766839.0 claiming benefit of PCT/US2012/056606 claiming benefit of US Appl. No. 13/242,106, filed Sep. 23, 2011.

(Continued)

*Primary Examiner* — Imani Hayman
(74) *Attorney, Agent, or Firm* — Harness Dickey

(57) ABSTRACT

An irrigation system for a surgical instrument includes an irrigation tube arranged to convey an irrigation fluid and an irrigation clip structurally arranged to receive a portion of the irrigation tube. The irrigation clip includes a proximal portion, a distal portion, a body portion, and an arm portion. The arm portion is structurally configured to selectively attach the irrigation clip to the surgical instrument and to bias the irrigation clip toward the surgical instrument with a biasing force. The irrigation clip includes a tube locking portion structurally arranged to cooperate with the surgical instrument to engage the outer surface portion of the irrigation tube to inhibit rotation and axial displacement of the irrigation tube relative to the irrigation clip in response to the biasing force.

19 Claims, 9 Drawing Sheets

(56) References Cited

U.S. PATENT DOCUMENTS

| | | | |
|---|---|---|---|
| 4,997,421 A | 3/1991 | Palsrok et al. |
| 5,019,038 A | 5/1991 | Linden |
| 5,055,100 A | 10/1991 | Olsen |
| 5,085,657 A | 2/1992 | Ben-Simhon |
| 5,147,203 A | 9/1992 | Seidenberg |
| 5,162,044 A | 11/1992 | Gahn et al. |
| 5,224,944 A | 7/1993 | Elliott |
| 5,312,327 A | 5/1994 | Bales et al. |
| 5,336,220 A | 8/1994 | Ryan et al. |
| 5,451,222 A | 9/1995 | De Maagd et al. |
| 5,460,490 A | 10/1995 | Carr et al. |
| D373,190 S | 8/1996 | Monson |
| 5,624,393 A | 4/1997 | Diamond |
| D384,148 S | 9/1997 | Monson |
| 5,695,461 A | 12/1997 | Schaible |
| 5,792,167 A | 8/1998 | Kablik et al. |
| 5,928,257 A | 7/1999 | Kablik et al. |
| 5,947,972 A | 9/1999 | Gage et al. |
| 5,989,212 A | 11/1999 | Sussman et al. |
| 5,997,499 A | 12/1999 | Sussman et al. |
| 6,030,356 A | 2/2000 | Carlson et al. |
| 6,080,128 A | 6/2000 | Sussman et al. |
| 6,110,162 A | 8/2000 | Sussman et al. |
| 6,146,353 A | 11/2000 | Platt, Jr. |
| 6,179,805 B1 | 1/2001 | Sussman et al. |
| 6,256,859 B1 | 7/2001 | Stoddard et al. |
| 6,287,274 B1 | 9/2001 | Sussman et al. |
| 6,342,061 B1 | 1/2002 | Kauker et al. |
| 6,398,759 B1 | 6/2002 | Sussman et al. |
| 6,575,929 B2 | 6/2003 | Sussman et al. |
| 6,579,270 B2 | 6/2003 | Sussman et al. |
| 6,589,204 B1 | 7/2003 | Sussman et al. |
| 6,648,847 B2 | 11/2003 | Sussman et al. |
| 6,676,628 B2 | 1/2004 | Sussman et al. |
| 6,689,146 B1 | 2/2004 | Himes |
| 6,783,520 B1 | 8/2004 | Candray et al. |
| 6,860,868 B1 | 3/2005 | Sussman et al. |
| 7,122,035 B2 | 10/2006 | Canady |
| 7,422,582 B2 | 9/2008 | Malackowski et al. |
| 7,621,911 B2 | 11/2009 | Ariola, Jr. |
| 7,632,079 B2 | 12/2009 | Hershberger et al. |
| 7,717,931 B2 | 5/2010 | Himes |
| 7,753,880 B2 | 7/2010 | Malackowski |
| 2002/0087179 A1 | 7/2002 | Culp et al. |
| 2005/0090777 A1 | 4/2005 | Carter |
| 2005/0245898 A1 | 11/2005 | Wright et al. |
| 2007/0250098 A1 | 10/2007 | Malackowski et al. |
| 2010/0234867 A1 | 9/2010 | Himes |

OTHER PUBLICATIONS

International Search Report and Written Opinion dated Jan. 25, 2013 for PCT/US2012/056606 claiming benefit of U.S. Appl. No. 13/242,106, filed Sep. 23, 2011.

International Preliminary Report on Patentability and Written Opinion dated Apr. 3, 2014 for PCT/US2012/056606 claiming benefit of U.S. Appl. No. 13/242,106, filed Sep. 23, 2011.

IRRIGATION SYSTEM AND CLIP FOR A SURGICAL INSTRUMENT

CROSS-REFERENCE TO RELATED APPLICATIONS

This application is a continuation of U.S. patent application Ser. No. 13/242,106 filed on Sep. 23, 2011. The entire disclosures of the above applications are incorporated herein by reference.

FIELD

This disclosure is directed to a surgical system and a system and method for attaching an irrigation system to a surgical instrument to direct irrigating fluid to a surgical site.

BACKGROUND

Many surgical procedures, such as those using cutting elements, generate heat at the surgical site due to friction at the cutting element and bone interface. Irrigation fluids may be introduced to the surgical site to cool the tissue being treated or to cleanse or wash tissue or debris from the surgical area. Some surgical instruments that may be used in these procedures do not have built in irrigation capability. Accordingly, when surgeries requiring irrigation are performed using these instruments, a separate irrigation hose is used and held at the irrigation site. In some instances, the surgeon will hold the surgical instrument with one hand, while holding the irrigation hose with the other hand. Preferably, the surgeon holds the instrument while an assistant holds the irrigation hose. Accordingly, in these instances, the surgeon must hold two instruments or must use an assistant, increasing the complexity of the procedure. In addition, during these procedures, the surgeon may adjust the instrument to best perform the procedure, and the instrument may move in and out of the irrigation stream, potentially resulting in momentary hot-spots and creating variation and inconsistency in cooling.

Since even moderate fluctuations in temperatures can introduce necrosis, surgeons try to direct the irrigation fluid directly at the location that will be most effective in cooling the instrument and the tissue. Some surgical instruments are designed to accept different cutting tools particularly designed for particular applications. Depending on the application, the stage of the surgery, and the particular cutting tool, the surgeon's desired irrigation location may be different relative to the surgical instrument body during the procedure, making even fixed irrigation systems unsuitable when used with incompatible instruments.

The present disclosure is directed to a system that attaches an irrigation tube to a surgical instrument, and that is easily adjustable to modify or redirect the flow of fluid during a surgical procedure. The systems and methods disclosed herein address one or more of the limitations in the prior art.

SUMMARY

In one exemplary aspect, the present disclosure is directed to an irrigation system for a surgical instrument. The system includes an irrigation tube arranged to convey an irrigation fluid. The irrigation tube has an outer surface portion. The system also includes an irrigation clip structurally arranged to receive a portion of the irrigation tube. The irrigation clip includes a proximal portion, a distal portion, a body portion, and an arm portion. The arm portion is structurally configured to selectively attach the irrigation clip to the surgical instrument and to bias the irrigation clip toward the surgical instrument with a biasing force. The irrigation clip includes a tube locking portion structurally arranged to cooperate with the surgical instrument to engage the outer surface portion of the irrigation tube to inhibit rotation and axial displacement of the irrigation tube relative to the irrigation clip in response to the biasing force.

In one aspect, the tube locking portion comprises a tube-receiving slot formed in the body portion and disposed to face the surgical instrument when the irrigation clip is attached to the surgical instrument. The portion of the irrigation tube being disposed within the slot.

In one aspect, a projecting locking feature is disposed in the tube receiving slot. The irrigation tube is disposed within the tube receiving slot so that when the irrigation clip is attached to the surgical instrument, a portion of the outer surface of the irrigation tube presses against the surgical instrument to selectively clamp the irrigation tube between the surgical instrument and the projecting locking feature.

In one aspect, the tube locking portion comprises a locking tab displaceable relative to the body portion in response to the biasing force. The locking tab is arranged to engage and inhibit rotation and axial displacement of the surgical tube relative to the irrigation clip in response to the biasing force.

In another exemplary aspect, the present disclosure is directed to an irrigation system for connection to a surgical instrument. The irrigation system includes a body having a distal portion and a proximal portion. The proximal portion is configured to receive irrigation tubing. The body includes an outer side and an inner side, with the inner side configured to face the surgical instrument when the body is connected to the surgical instrument. The inner side includes an opening therein forming a tube receiving slot configured to receive the irrigation tubing. The system includes means in the slot for engaging irrigation tubing within the slot and inhibiting rotation and axial displacement of irrigation tubing. A first set of arms extends from the body. The arms are flexible and spaced apart to elastically flex when being applied around the surgical instrument and to snap onto the surgical instrument to bias the irrigation clip toward the surgical instrument with a biasing force.

In another exemplary aspect, the present disclosure is directed to a method of directing irrigating fluid with an irrigation system and a surgical instrument. The method includes rationally and axially adjusting an irrigation tube disposed within an irrigation clip to a desired location, and clamping the irrigation tube between a portion of the irrigation clip and the surgical instrument to inhibit further rotational and axial displacement of the irrigation tube relative to the irrigation clip by snapping the irrigation clip onto the surgical instrument.

BRIEF DESCRIPTION OF THE DRAWINGS

A more complete understanding of the present disclosure and advantages thereof may be acquired by referring to the following description taken in conjunction with the accompanying figures.

DETAILED DESCRIPTION OF THE DRAWINGS

Reference is now made in detail to exemplary embodiments of the invention, examples of which are illustrated in the accompanying drawings. Wherever possible, the same reference numbers are used throughout the drawings to refer to the same or like parts.

The present disclosure is directed to a surgical system usable in surgical procedures that provides increased irrigation capability and convenience. It provides cooling irrigation fluid to a surgical site during surgical treatments. The surgical system includes a surgical instrument and a removable irrigation system on the surgical instrument that is designed to easily attach to the surgical instrument for stability and consistency in irrigation cooling, yet can be easily adjusted by the surgeon to direct the irrigation fluid as desired.

Figure 1:
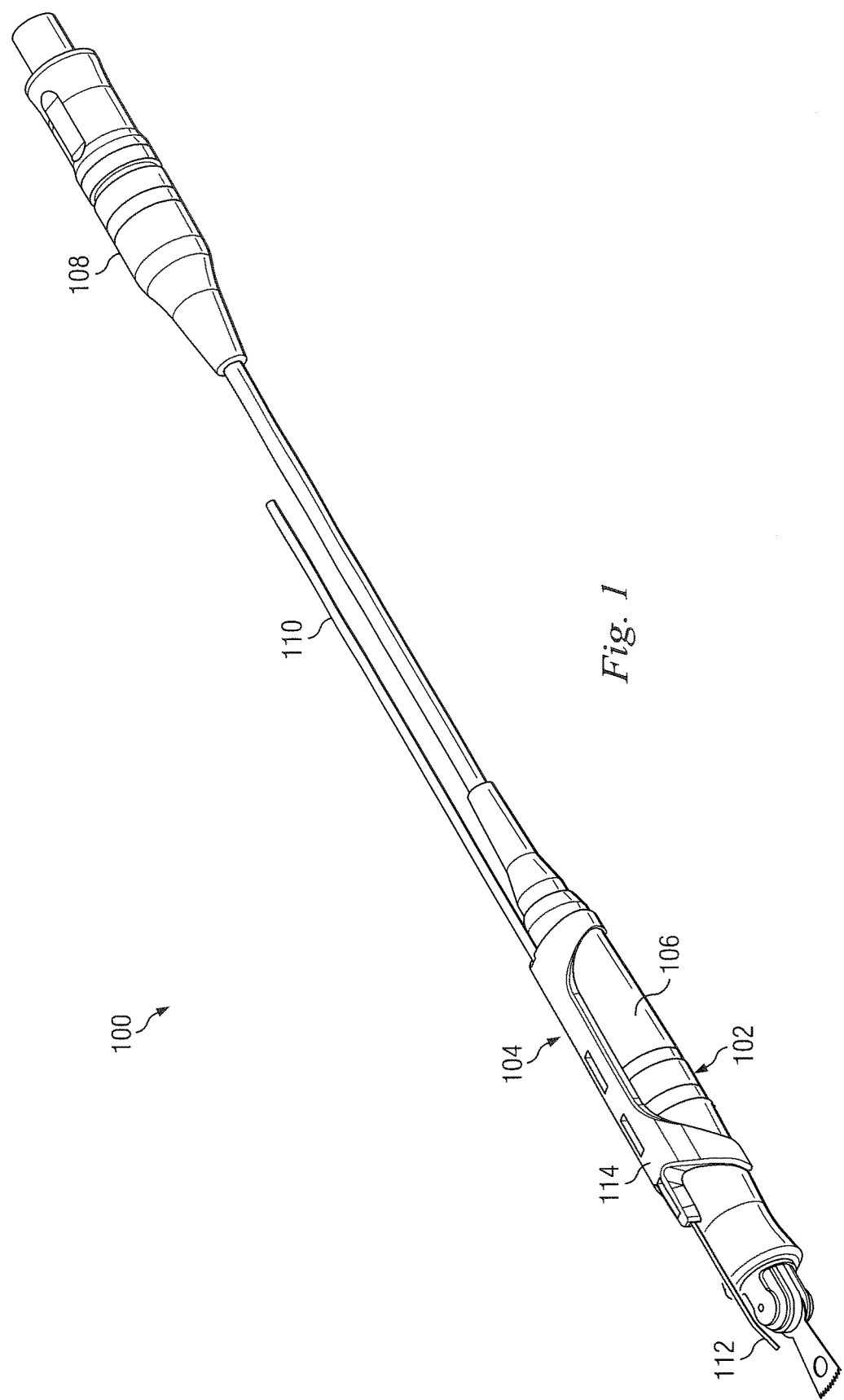
FIG. 1 is an illustration of an exemplary surgical system including a surgical instrument and an irrigation system in accordance with one aspect of this disclosure.

FIG. 1 depicts a surgical system 100 in accordance with one exemplary aspect including a surgical instrument 102 and an irrigation system 104. In this example, the surgical instrument 102 is a sagittal surgical saw that may be used to cut bone during surgical procedures. However, in other examples, the surgical instrument 102 is type of surgical instrument other than a saw that may be used in procedures where irrigation is desirable. The surgical instrument 102 has a cylindrical body portion 106 that carries the irrigation system 104. In one embodiment, the cylindrical body portion 106 may correspond with a handle or gripping portion of the surgical instrument 102. In this example, the surgical instrument 102 may be configured to attach to a surgical console (not shown) via a plug 108 extending from a proximal end. In this example, the surgical instrument is free of hand-control components and may be operated by a foot pedal or other control connected to or forming a part of a surgical console.

The irrigation system 104 includes a flexible irrigation tube 110, an irrigation tip 112, and an irrigation clip 114. The irrigation system 104 is selectively attachable to the surgical instrument 102 to affix the irrigation tip 112 relative to the instrument. This enables a surgeon to control the direction of the fluid flow during irrigation processes. In addition, with the irrigation system 104 connected to the surgical instrument 102, the surgeon may hold both the instrument and the irrigation system using the same hand. The components of the irrigation system 104 are shown and described in greater detail in the paragraphs below.

Figure 2:
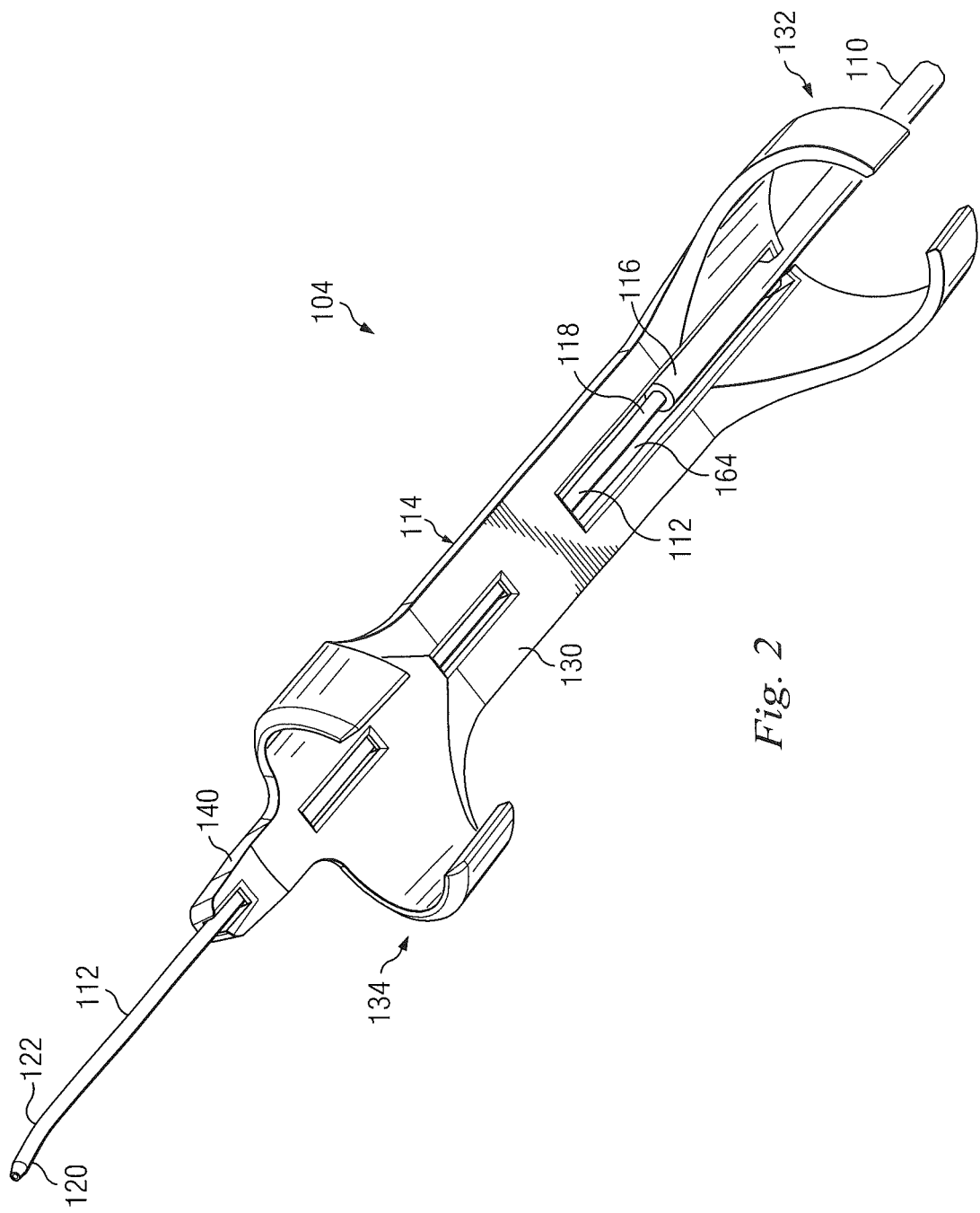
FIG. 2 is an illustration of the exemplary irrigation system of FIG. 1 in accordance with one aspect of this disclosure.
Figure 3:
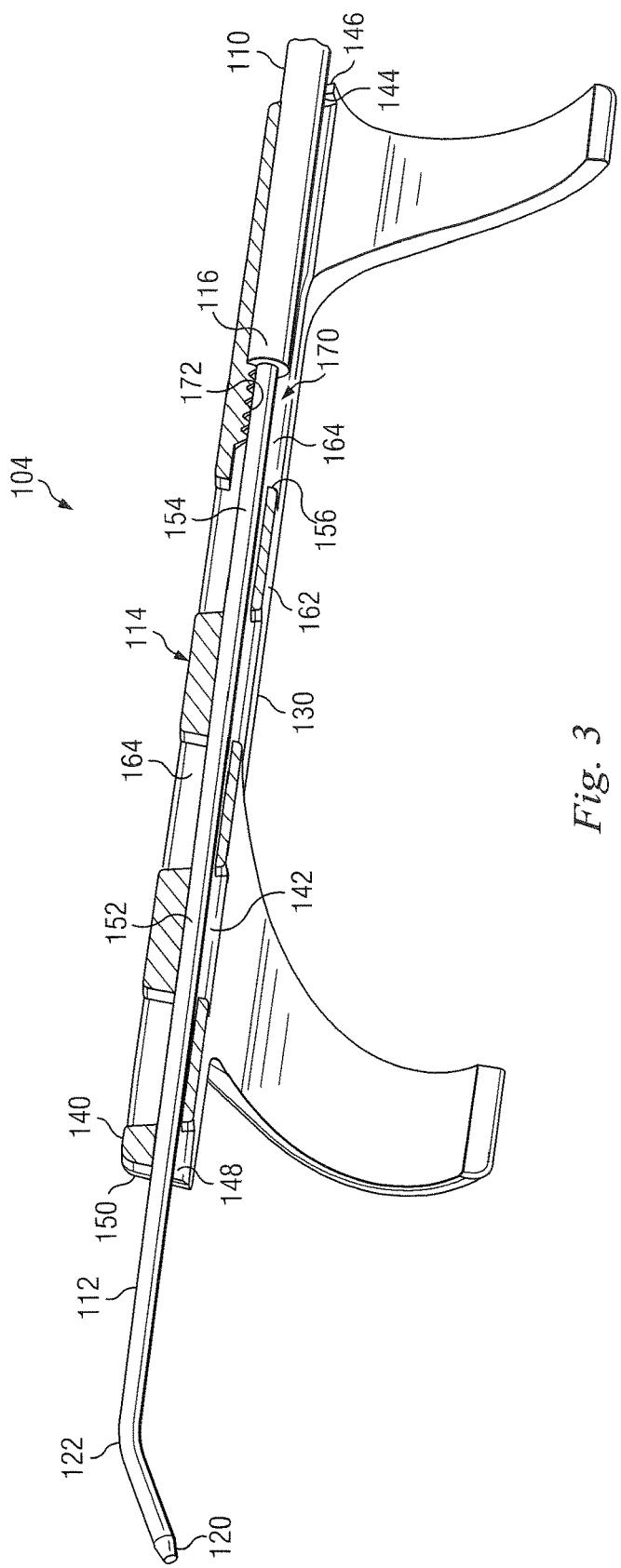
FIG. 3 is an illustration of a cross-sectional view of the exemplary irrigation system of FIG. 1 in accordance with one aspect of this disclosure.

FIG. 2 shows the irrigation system 104 in full view and FIG. 3 shows the irrigation system in cross-section. As can be seen, the irrigation tube 110 extends from the irrigation clip 114. The irrigation tube 110 is a standard, flexible surgical irrigation tube that extends from a fluid source at a proximal end (not shown) to a distal end 116 at the irrigation clip 114. It includes an inner diameter, an outer diameter, and an outer surface. In one example, the irrigation 110 tube has a length greater than, for example, ten feet, and can extend from the fluid source to the surgical instrument 102 at a surgical site.

The irrigation tip 112 is connected to and extends from the distal end 116 of the irrigation tube 110. Its narrow inner diameter provides the surgeon with more directed control of the irrigation fluid as it flows onto the instrument blade and the surgical site. The irrigation tip 112 includes a proximal end 118 and a distal end 120. The proximal end 118 may be attached to the distal end 116 of the irrigation tube 110 using any known method or system. For example, the irrigation tip 112 is shown here as extending at least partially into the lumen formed by the inner diameter of the irrigation tube 110. In one embodiment, the irrigation tip 112 is attached to the irrigation tube 110 using an adhesive. In another embodiment, the irrigation tip 112 is formed as an integral part or a monolith part of the tube 110 itself.

In the example shown, the irrigation tip 112 is formed of a metal material and is annealed at a distal portion 122 adjacent the distal end 120 so that it is malleable and can be bent at a desired angle to direct the fluid flow. In this example, only the distal portion 122 of the irrigation tip 112 is so annealed, such that the remainder of the tip 112, including the proximal end 118, is more rigid. This provides additional sturdy support for the distal region of the tip 112. In use, the irrigation tip 112 extends from a distal tip of the irrigation clip 114, and it may telescope relative to the clip 114, along with the irrigation tube 110, to enable the health care provider to precisely position it for irrigation.

Figure 4:
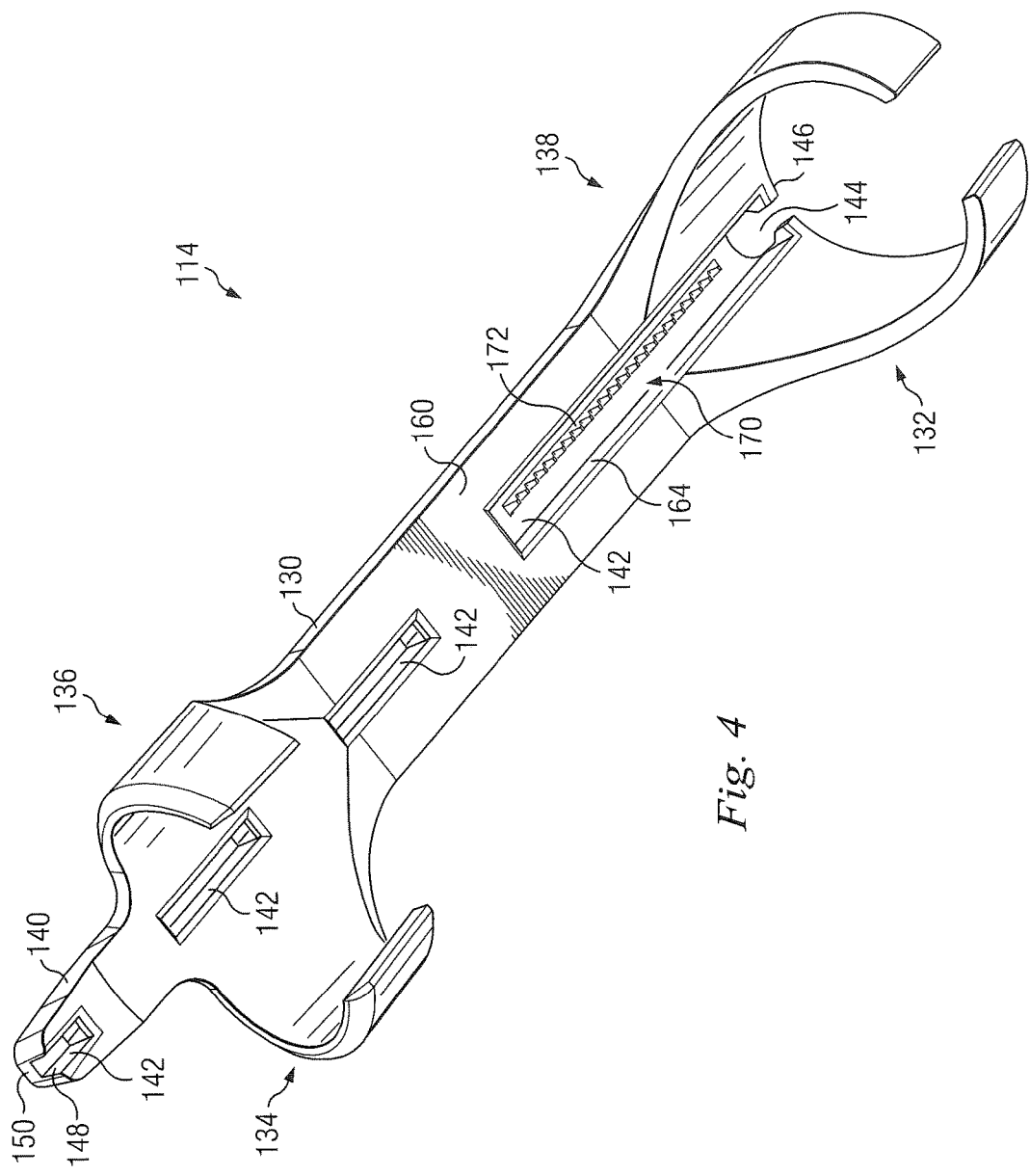
FIG. 4 is an illustration of an exemplary irrigation clip of the irrigation system of FIG. 1 in accordance with one aspect of this disclosure.

FIGS. 2-4 all illustrate the irrigation clip 114. The irrigation clip 114 is arranged to clip onto the exterior surface of the surgical instrument 102, such as the cylindrical body portion 106 of the surgical saw shown in FIG. 1. As can be seen, the irrigation clip 114 includes a body 130 and proximal and distal sets of arms 132, 134 extending from the body 130. The body 130 has a distal portion 136 and a proximal portion 138, with the distal set of arms 134 being disposed toward the distal portion 136 and the proximal set of arms 132 being disposed toward the proximal portion 138. The sets of arms elastically deflect or resiliently flex to snap the clip 114 onto the surgical instrument 102. A projecting neck 140 is disposed distal of the distal set of arms 134. The neck 140 is a rigid element that cooperates with and stabilizes the distal region of the irrigation tip 112.

As can be seen, the body 130 includes a passage 142 extending entirely therethrough with a proximal opening 144 at a proximal end 146 and with a distal opening 148 at a distal end 150. This may be best seen in the cross-sectional view in FIG. 3. Here, the passage 142 is formed between a series of spaced, alternatingly offset upper and lower passage walls. The proximal opening 144 is sized to receive the distal end 116 of the irrigation tube 110 therethrough, and the distal opening 148 is sized to receive the irrigation tip 112 therethrough. The proximal opening in this case is a C-shaped opening (FIG. 4) sized to permit the irrigation tube 110 to be inserted laterally therethrough by deformation under force, but by extending more than half the circumference around the irrigation tube 110, to mechanically restrict inadvertent removal. The distal opening 148 is formed by the offset upper and lower passage walls.

As shown in the cross-sectional view, the passage 142 extends from the proximal end 146 to the distal end 150. The passage 142 has a distal portion 152 with a relatively smaller width or diameter and a proximal portion 154 with a relatively larger width or diameter. In use, the distal portion 152 is sized to provide a relatively stable fit with the irrigation tip 112, while still permitting axial movement in both the proximal and distal directions. This permits a surgeon to adjust the irrigation tip 112 telescopically relative to the clip 114. When the irrigation tip 112 is fixed to the irrigation tube 110, the irrigation tube 110 likewise axially displaces relative to the clip 114. The proximal portion 154 is sized large enough to receive an end of the irrigation tube 110. In this embodiment, it is shown with a substantially square cross-section, however, other shapes are contemplated. A shoulder 156 separates the distal and proximal portions 152, 154 of the passage 142, and limits the axial movement of the irrigation tube 110 in the distal direction.

The body 130 includes an outer facing surface 160 and an opposing inner facing surface 162. The inner facing surface 162 is disposed to face the surgical instrument 102 when the irrigation clip 114 is attached the surgical instrument 102. An opening 164 in the inner facing surface 162 communicates with the proximal portion 154 of the passage 142 and permits access or communication with the irrigation tube 110 when the irrigation tube 110 is in the clip 114. This opening 164, combined with the passage 142, forms a tube locking portion arranged to cooperatively secure the irrigation tube 110 in place while limiting rotational movement of the clip 114 and tube 110. The tube locking portion includes a tube locking slot 170 formed by the opening 164 and the passageway 142. The slot 170 extends axially along a portion of the body 130 and, as discussed further below, cooperatively secures the irrigation tube 110 in place while limiting rotational movement of the clip 114 and tube 110.

locking feature 172 is disposed within the tube locking slot 170. In this example, the locking feature 172 is formed of an axially extending structure disposed within a bottom of the tube locking slot 170, facing in the direction of the inner facing surface 162, and is configured to engage a portion of the irrigation tube 110 within the slot 170. In this example, the locking feature 172 comprises a series of serrations formed in a line. These serrations form a series of distally angled teeth and are configured to engage the outer surface for the irrigation tube 110 to inhibit axial movement of the irrigation tube 110 in the proximal direction, opposite the angled teeth. In one example, the distance from the inner facing surface 162 to the serrations is less than the width or outer diameter of the irrigation tube. As such, the irrigation tube may be disposed on the serrations, and protrude slightly out of the slot 170.

In this embodiment, the serrated locking feature 172 is integral with and molded as a part of the clip 114 itself. It is arranged to impinge upon the flexible irrigation tube and immobilize the irrigation tube 110 between the clip body 130 and the surgical instrument 102 when the clip 114 is on the surgical instrument 102. Because of the serrated locking teeth, the locking feature 172 prevents both rotation and axial displacement. Accordingly, the flexible irrigation tube 110 is secured in place in the passage 142. The likewise secures the irrigation tip 112 in place when the tip 112 is fixed to the tube 110.

The distal set of arms 134 and the proximal set of arms 132 extend from the body 130 in oblique directions. Each set of arms 132, 134 has two arms 180, each having an arm end 182. The sets of arms 132, 134 form a C-shape and have a curvature forming a diameter slightly or smaller than the diameter of the surgical instruments. The arms 180 are also elastically resilient so that the instrument 102 may be pressed between the arms 180, forcing the arms 180 to separate to receive the instrument 102, and then snap onto the instrument 102 as the instrument maximum diameter passes the arm ends 182. Because of the resilient nature of the arms 180, the arms 180 can tightly grip the instrument 102, securing the clip 114 in place, yet still be easily removed from or displaced along the instrument 102. The arms 180 compliant or flexible nature of the arms provide a biasing or pulling force when on the instrument 102 that pulls the body 130 close to and against the instrument 102. This pulling force 102 is also the same force used to secure the irrigation tube 110 in place in the clip and in place relative to the surgical instrument 102.

The irrigation clip 114 may be formed of any number of materials, but is preferably a resilient material, such as for example, a polymer material. In one embodiment, it is a molded element as a single monolith. In another embodiment, the irrigation clip 114 is formed with a body and with arms that are separate elements, attached together. In different embodiments, the clip may be machined or molded and may be formed of any material includes polymers and metals.

Figure 5:
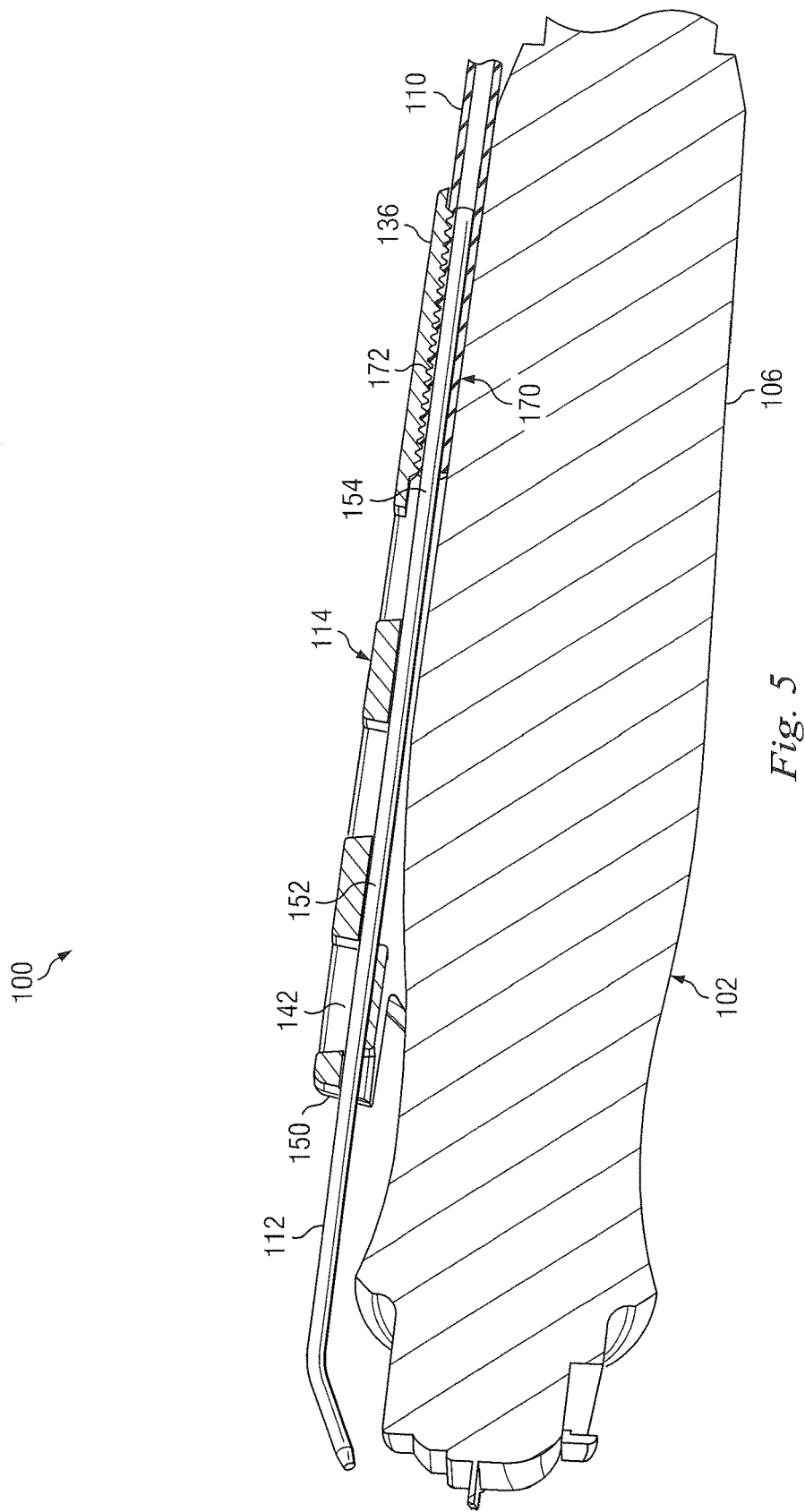
FIG. 5 is an illustration of an exemplary cross-sectional view of the exemplary surgical system of FIG. 1 in accordance with one aspect of this disclosure.

FIG. 5 shows the surgical system 100 in cross-section with the irrigation system 104 attached to the instrument 102 in a manner securing the irrigation tube 110 in place. In use, the distal tip 112 and the irrigation tube 110 are introduced through the proximal end of the clip 114, and the distal tip 112 is fed through the distal portion 152 of the passage 142 and out the distal end 150 of the clip 114. The irrigation tube 110 is disposed in the proximal portion 154 of the passage 142, and is in contact with the locking feature 172 on one side of its outer surface. Its opposing side is adjacent the opening forming the locking slot 170 in the inner surface 162, and in some embodiments, projects at least slightly outward through the top of the locking slot 170. When the clip 114 is snapped onto the surgical instrument 102, the resilient proximal and distal sets of arms 132, 134 cooperate with the curved surfaces of the surgical instrument to apply a biasing force on the instrument 102 that pulls the body 130 toward the instrument 102 so that the irrigation tube 110 at the locking slot 170 comes into contact with and engages the surgical instrument 102. As such, the irrigation tube 110 is in contact with and compressively clamped between the locking features 172 on one side and the surgical instrument body 106 on the opposing side. With the biasing force pulling the body 130 toward the instrument 102, the locking features 172 frictionally engage and prevent relative movement of the irrigation tube 110. The angle of the locking features 172 provides additional resistance to proximal movement so that the irrigation tube 110 will not inadvertently pull out from the irrigation clip 114 during standard use. The irrigation clip 114 is held in place by the frictional resistance of the irrigation tube 110 and the biasing force of the sets of legs 132, 134. Thus, the irrigation tube 110 is secured in place relative to the irrigation clip 114 and the instrument body 106 both axially and rotationally.

The surgeon may adjust the irrigation system 104 by lifting the proximal portion 136 of the irrigation clip 114 to remove the clamping loading on the irrigation tube 110. This may be done by simply raising the proximal portion 136 to remove loading on the irrigation tube 110 without fully disengaging the proximal set of arms 132, or may include fully disengaging the proximal set of arms 132 from the surgical instrument 102. With the loading removed, the irrigation tube 110 may be axially advanced or retracted along the locking features 172, resulting in a telescoping of the irrigation tip 112 relative to the irrigation clip 114. The irrigation tube 110 may be rotated as well so that the irrigation tip 112 is aimed as desired. When the surgeon is satisfied, he may push downward on the clip 114 to reengage the proximal arms 132 about the instrument 102, thereby reengaging the clamping force on the irrigation tubing 110 between the locking features 172 and the surgical instrument 102. Also, at any time, the surgeon may manipulate the malleable distal portion 122 of the irrigation tip 112 to aim the irrigating fluid as desired.

Figure 6:
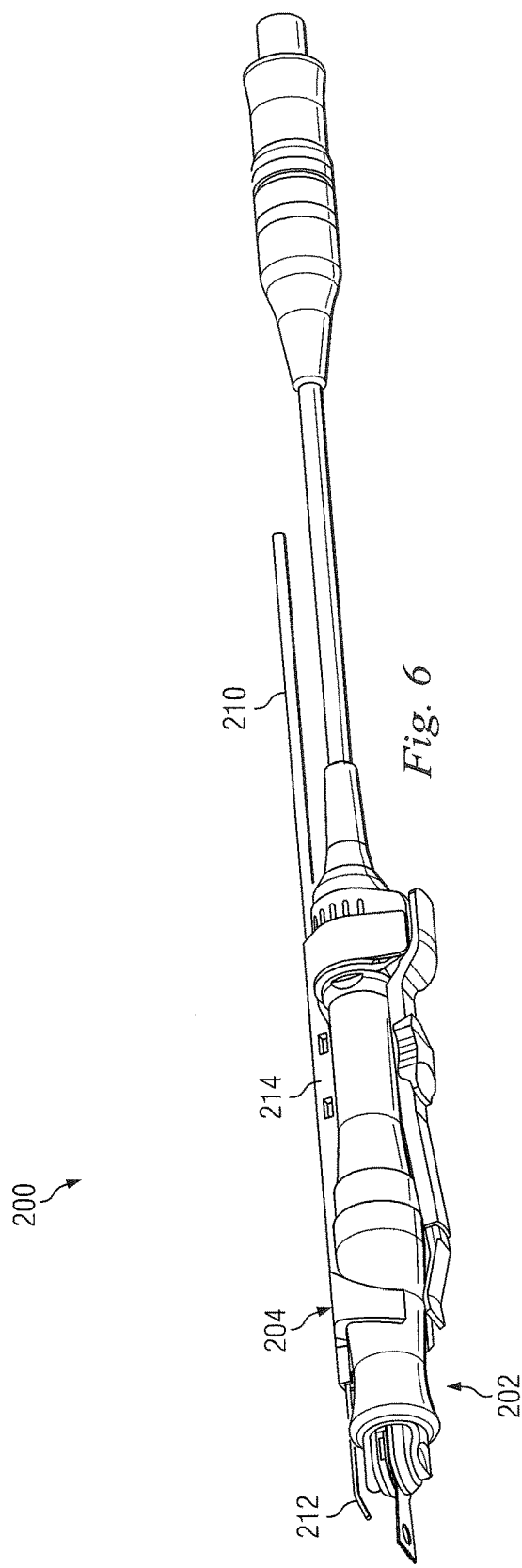
FIG. 6 is an illustration of another exemplary surgical system including a surgical instrument and an irrigation system in accordance with one aspect of this disclosure.
Figure 7:
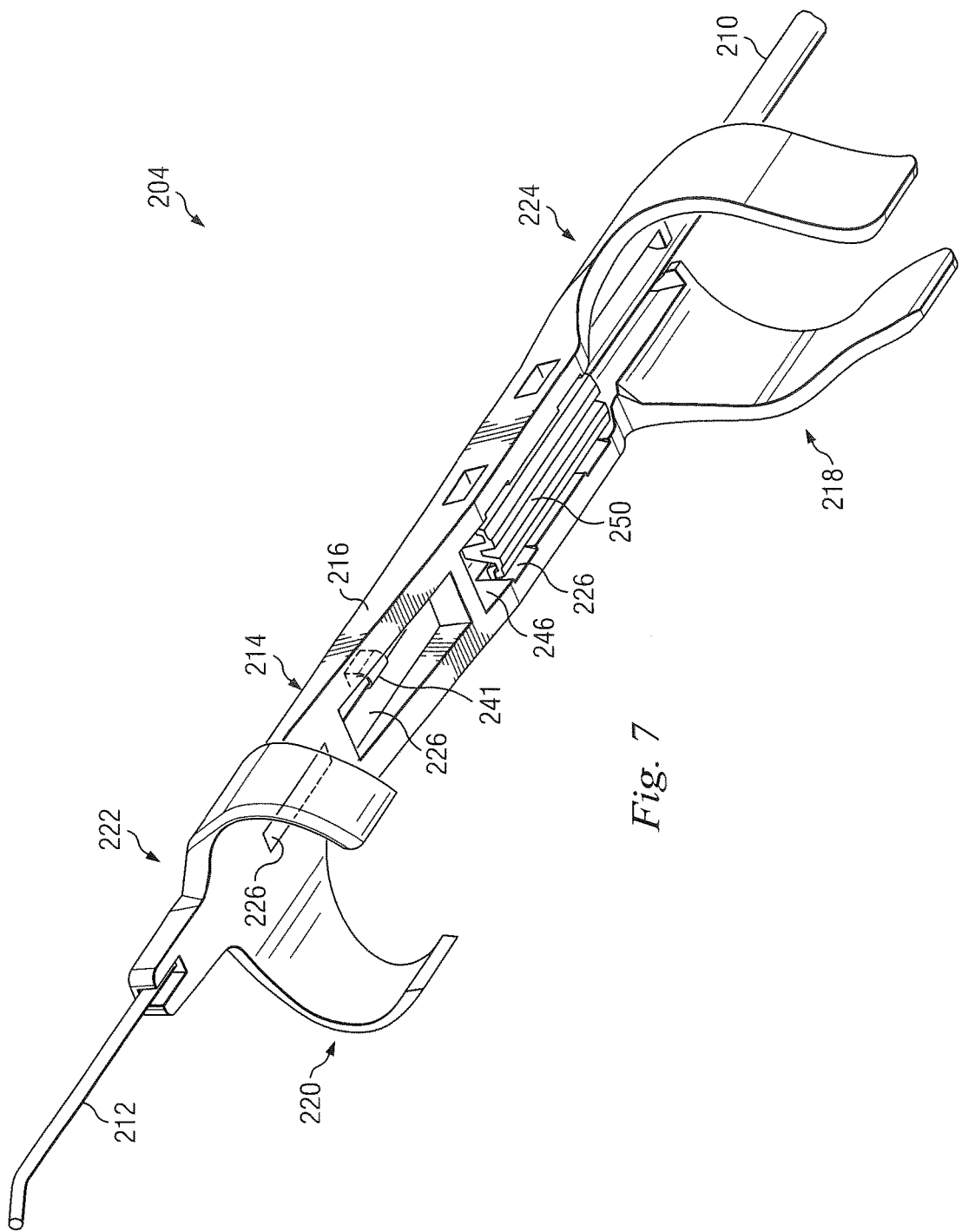
FIG. 7 is an illustration of the exemplary irrigation system of FIG. 6 in accordance with one aspect of this disclosure.
Figure 8:
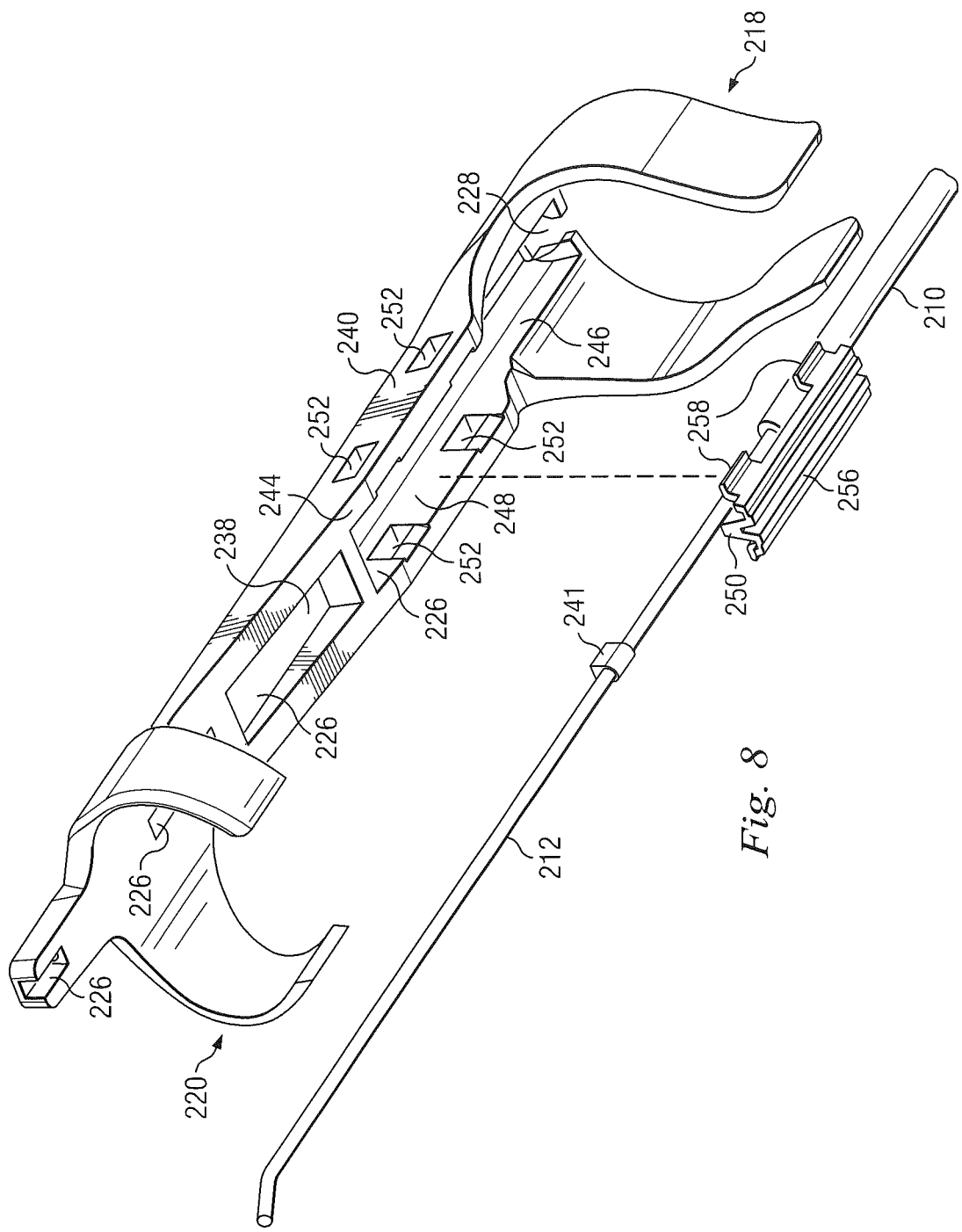
FIG. 8 is an illustration of an exemplary partially exploded view of the irrigation system of FIG. 6 in accordance with one aspect of this disclosure.

FIG. 6 shows a second embodiment of a surgical system, referenced by the numeral 200. The irrigation system 200 includes many of the same features as the surgical system 100 as discussed above, and for the sake of simplicity, not all the features will be re-described. It is to be understood that any portion of the description of the irrigation system 100 may equally apply to the irrigation system 200.

The surgical system 200 includes a surgical instrument 202 and an irrigation system 204. Here, the surgical instrument 202 is shown as a reciprocating surgical saw, and in this example, the surgical instrument includes hand-control components, including an operating lever 206.

Figure 9:
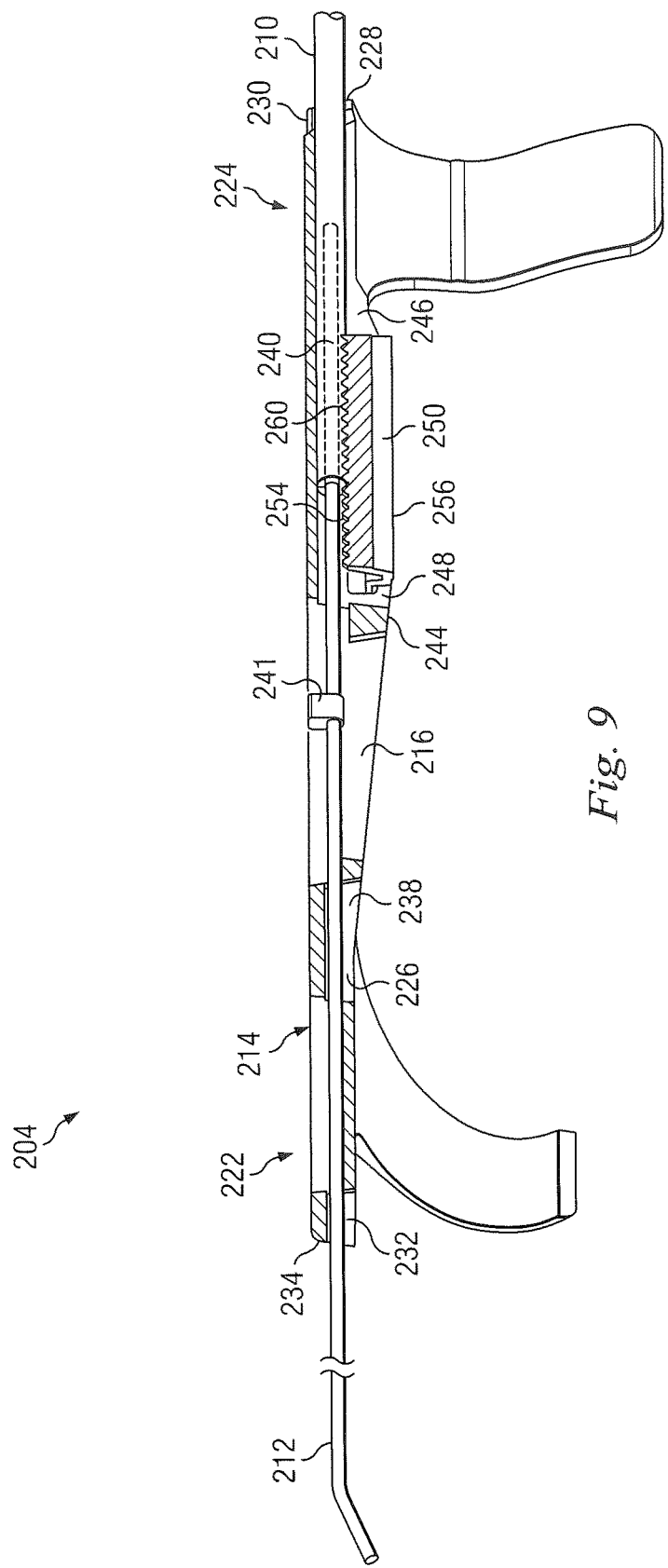
FIG. 9 is an illustration of an exemplary cross-sectional view of the irrigation system of FIG. 7 in accordance with one aspect of this disclosure.

The irrigation system 204 includes a flexible irrigation tube 210, an irrigation tip 212, and an irrigation clip 214. Similar to the clip 114 described above, the irrigation clip 214 comprises a body 216 and proximal and distal sets of arms 218, 220, respectively disposed at a proximal and distal portions 222, 224. The body 216 includes a passage 226 extending entirely therethrough with a proximal opening 228 at a proximal end 230 and with a distal opening 232 at a distal end 234. This may be best seen in the cross-sectional view in FIG. 9. Here, the passage 226 is formed between a series of spaced, alternatingly offset upper and lower passage walls. The proximal opening 228 is sized to receive a distal end of the irrigation tube 210 therethrough, and the distal opening 232 is sized to receive the irrigation tip 212 therethrough. The distal opening 232 is formed by the offset upper and lower passage walls.

As shown in the cross-sectional view, the passage 226 extends from the proximal end 230 to the distal end 234. The passage 226 has a distal portion 238 with a relatively smaller width or diameter and a proximal portion 240 with a relatively larger width or diameter. Like the embodiment described previously, the distal portion 238 is sized to provide a relatively stable fit with the irrigation tip 212, while still permitting axial movement in both the proximal and distal directions. This permits a surgeon to adjust the irrigation tip 212 telescopically relative to the clip 214. The proximal portion 240 is sized large enough to receive the irrigation tube 210.

A slide stop 241 is disposed in the distal portion 238 of the passage 226. The slide stop 241 is fixed to the irrigation tip 212 and is configured to axially slide with the irrigation tip 212. Here, the slide stop is disposed between two spaced walls that limit the axial travel of the irrigation tip 212 to a telescopic range between about 0.25 and 4 inches in one embodiment, and between about 0.5 and 4 inches in another embodiment. Other ranges, both higher and lower, are contemplated.

The body 216 includes an inner facing surface 244 disposed to face the surgical instrument 202 when the irrigation clip 214 is attached thereto. An opening 246 to a tube locking slot 248 in the inner facing surface 244 communicates with the proximal portion 240 of the passage 226 and permits access or communication with the irrigation tube 210 when the irrigation tube 210 is in the clip 214. This opening 246, combined with the passage 226, forms a tube locking portion arranged to cooperatively secure the irrigation tube 210 in place while limiting rotational movement of the clip 214 and tube 210.

In this embodiment, the tube locking portion includes the tube locking slot 248 and a locking tab 250. The tube locking slot 248 extends into the body 216 from the opening 246, forms all or a part of the proximal portion of the passage 240, and in this example, includes lateral or side openings 252 that cooperate with the locking tab 250 to prevent inadvertent removal.

The locking tab 250, in this example, fits partially or fully into the opening 246 and is configured to clamp the irrigation tube 210 against the bottom of the slot 248 to prevent rotational or axial movement of the tube 210 relative to the clip 214. The locking tab 250 includes a locking surface 254 and an opposing instrument engaging surface 256. Stops 258 extend from lateral sides of the locking tab 250 and are configured to extend into the side openings 252 of the tube locking slot 248. These stops 258 and openings 252 secure the locking tab 250 within the slot 248 and prevent the locking tab 250 from inadvertently displacing or falling out of the slot 248. However, the stops 258 and openings 252 are sized to allow a level of displacement of the locking tab 250 sufficient to remove loading enough to enable adjustment of the irrigation tube 210 within the passage, and sufficient to load by clamping the irrigation tube 210 within the slot 248 to inhibit or prevent rotational or axial displacement under normal operational loads that may be applied to the irrigation tubing during use. Thus, the locking tab 250 may be configured to cooperate with the slot 248 to move laterally to engage the irrigation tube in the slot with adjustable levels of force. The locking tab 250 is sized to protrude at least partially out of the opening 246 to engage the surgical instrument 202 when the clip 214 is connected to the surgical instrument 202.

The locking surface 254 of the locking tab 250, in this embodiment, includes a locking feature 260. Here, the locking feature 260 includes serrations or teeth projecting directly transverse to or substantially normal to the irrigation tube 110. However, as is apparent, other embodiments include angled projections, as described above with reference to the locking feature 172 described above. The locking feature 260 is configured to engage the outer surface for the irrigation tube 110 to inhibit axial and rotational movement of the irrigation tube 110 to secure the irrigation tube in the passage 226.

Like the sets of arms described above, the proximal set of arms 218 and the distal set of arms 220 extend from the body 216 and form a C-shape. They are also elastically resilient so that the instrument 202 may be pressed between the arms, forcing them to separate to receive the instrument 202 and then snap the clip 214 onto the instrument 202, both holding the clip 214 in place and providing a biasing or pulling force that pulls the body 216 close to and against the instrument 202. This pulling force presses the locking tab 250 against the surgical instrument 202, forcing it further into the slot 248 and against the irrigation tube 210, clamping the irrigation tube 210 against the locking feature 260 and the bottom of the slot 248.

The disclosure of a method of use and adjusting the tube 210 is the same as described above, recognizing that the locking tab 250 is disposed between the irrigation tube 210 and the surgical instrument. When the loading is removed, the locking tab 250 displaces, loosening the clamping effect, permitting easier rotation and axial movement of the irrigation tube 210.

It is evident that the particular illustrative embodiments disclosed above may be altered or modified and all such variations are considered within the scope and spirit of the present invention.

What is claimed is:

1. An irrigation system for a surgical instrument, comprising:
   a body extending from a proximal end to a distal end and defining a passage extending along the body to receive an irrigation tube, the body having an inner side configured to face the surgical instrument and an opposed outer side;
   a first set of connecting arms extending from the body and configured to connect the body and the irrigation tube to the surgical instrument;
   a second set of connecting arms extending from the body and configured to connect the body and the irrigation tube to the surgical instrument, wherein the first set of connecting arms is positioned at the proximal end of the body and the second set of the connecting arms is positioned at the distal end of the body; and
   an irrigation tube locking portion positioned relative to the passage and the irrigation tube, wherein the irrigation tube locking portion inhibits a movement of the irrigation tube relative to the body and the surgical instrument.

2. The irrigation system of claim 1, wherein the irrigation tube locking portion includes a locking feature having a plurality of projecting teeth configured to engage an outer surface of the irrigation tube.

3. The irrigation system of claim 2, wherein the plurality of projecting teeth are positioned within the passage of the body and configured to engage the irrigation tube upon connecting the body to the surgical instrument.

4. The irrigation system of claim 3, wherein the plurality of projecting teeth are formed as part of the body and project toward the surgical instrument upon attaching the body to the surgical instrument to capture the irrigation tube between the plurality of projecting teeth and the surgical instrument within the recess.

5. The irrigation system of claim 3, wherein the plurality of projecting teeth are disposed on a removable locking tab configured to be removably coupled to the body and relative to the passage.

6. The irrigation system of claim 5, wherein the locking tab includes stops configured to be received within openings in the body positioned relative to the passage to removably retain the locking tab with the body.

7. The irrigation system of claim 1, wherein the passage includes a proximal portion and a distal portion separated by a shoulder, the distal portion configured to receive an irrigation tip and the proximal portion configured to receive an end of the irrigation tube.

8. The irrigation system of claim 1, wherein the movement is rotation and axial displacement of the irrigation tube.

9. The irrigation system of claim 1, further comprising the surgical instrument and the irrigation tube.

10. An irrigation system for a surgical instrument, comprising:
    a body extending from a proximal end to a distal end and defining a passage extending along the body to receive an irrigation tube, the body having an inner side configured to face the surgical instrument and an opposed outer side;
    a first set of connecting arms extending from the body and configured to connect the body and the irrigation tube to the surgical instrument;
    an irrigation tube locking portion positioned relative to the passage and the irrigation tube, wherein the irrigation tube locking portion inhibits a movement of the irrigation tube relative to the body and the surgical instrument; and
    a slide stop configured to be disposed on an irrigation tip and configured to axially slide with the irrigation tip within a distal portion of the passage.

11. An irrigation system for a surgical instrument, comprising:
    a body extending from a proximal end to a distal end and defining a passage extending along the body to receive an irrigation tube, the body having an inner side configured to face the surgical instrument and an opposed outer side;
    a first set of connecting arms extending from the body and configured to connect the body and the irrigation tube to the surgical instrument;
    an irrigation tube locking portion positioned relative to the passage and the irrigation tube, wherein the irrigation tube locking portion inhibits a movement of the irrigation tube relative to the body and the surgical instrument; and
    wherein the passage is formed between a series of spaced, alternating offset upper and lower passage walls.

12. An irrigation system for a surgical instrument, comprising:
    a body extending from a proximal end to a distal end and having an inner side configured to face the surgical instrument in an opposed outer side;
    a first set of connecting arms extending from the body and configured to connect the body and an irrigation tube to the surgical instrument; and
    a second set of connecting arms extending from the body and configured to connect the body and the irrigation tube to the surgical instrument, wherein the first set of connecting arms is positioned at the proximal end of the body and the second set of the connecting arms is positioned at the distal end of the body; and
    an irrigation tube locking portion having a plurality of engaging projections positioned relative to the body and the irrigation tube to inhibit movement of the irrigation tube relative to the body and the surgical instrument.

13. The irrigation system of claim 12, wherein the body defines a passage extending along at least a portion of the body configured to receive at least a portion of the irrigation tube, wherein the irrigation tube locking portion is positioned adjacent to the passage.

14. The irrigation system of claim 13, wherein the plurality of engaging projections extend from the body and within the passage.

15. The irrigation system of claim 13, wherein the plurality of projections extend from a removable locking tab configured to be secured to the body adjacent to the passage.

16. The irrigation system of claim 12, wherein the plurality of engaging projections is configured to rotationally and axially retain the irrigation tube upon engaging the body to the surgical instrument.

17. An irrigation system for a surgical instrument, comprising:
    an irrigation tip configured to deliver an irrigation fluid to a surgical site;

an irrigation tube configured to be coupled to the irrigation tip to deliver the irrigation fluid from an irrigation source to the irrigation tip; and a securing clip configured to secure the irrigation tip and the irrigation tube to the surgical instrument, the securing clip having a body extending from a proximal end to a distal end and defining a passage extending along the body from the proximal end to the distal end to receive at least a portion of the irrigation tip and the irrigation tube, the irrigation tip extending from the distal end of the body and the irrigation tube extending into the proximal end of the body and coupled to the irrigation tube within the passage of the body;

wherein the securing clip is configured to retain the irrigation tip and the irrigation tube relative to the surgical instrument upon connecting the securing clip to the surgical instrument.

18. The irrigation system of claim 17, wherein the securing clip includes a locking feature extending in the passage and configured to engage at least an outer surface of the irrigation tube to inhibit movement of the irrigation tube relative to the surgical instrument.

19. The irrigation system of claim 18, wherein the locking feature further includes a plurality of engaging projections configured to engage the outer surface of the irrigation tube to inhibit rotational and axial movement of the irrigation tube relative to the surgical instrument.

* * * * *